US00PP21300P3

(12) United States Plant Patent
Campbell

(10) Patent No.: US PP21,300 P3
(45) Date of Patent: Sep. 21, 2010

(54) APPLE TREE NAMED 'CAMPBELL JONATHAN'

(50) Latin Name: *Malus domestica*
Varietal Denomination: Campbell Jonathan

(75) Inventor: Jeffrey Campbell, Waverly, MO (US)

(73) Assignee: International Plant Management Inc., Lawrence, MI (US)

( * ) Notice: Subject to any disclaimer, the term of this patent is extended or adjusted under 35 U.S.C. 154(b) by 196 days.

(21) Appl. No.: 12/287,618

(22) Filed: Oct. 14, 2008

(65) Prior Publication Data

US 2010/0095415 P1 Apr. 15, 2010

(51) Int. Cl.
*A01H 5/00* (2006.01)

(52) U.S. Cl. ..... Plt./166

(58) Field of Classification Search ..... Plt./166
See application file for complete search history.

(56) References Cited

U.S. PATENT DOCUMENTS

| | | | | | |
|---|---|---|---|---|---|
| PP2,650 | P | * | 7/1966 | Snyder | Plt./166 |
| PP2,934 | P | * | 10/1969 | Robison et al. | Plt./166 |
| PP5,086 | P | * | 8/1983 | Carnefix | Plt./166 |
| PP6,406 | P | * | 11/1988 | Higgins | Plt./166 |
| PP8,701 | P | * | 4/1994 | Thome | Plt./166 |
| PP10,115 | P | * | 11/1997 | Jackson et al. | Plt./166 |

* cited by examiner

*Primary Examiner*—Wendy C. Haas

(57) ABSTRACT

A new and distinct variety of Jonathan apple tree, 'Campbell Jonathan' originating as a limb mutation of the *Malus domestica* variety of 'Robison', (U.S. Plant Pat. 2,934). This new variety is unique from its parent and other Jonathan cultivars in that it has a very bold pattern of alternating dark red and bright red stripes on the skin of its fruit, unlike its parent which has very faint, thin stripes.

2 Drawing Sheets

Botanical designation: *Malus domestica.*
Variety denomination: 'Campbell Jonathan'.

DESCRIPTION OF RELATED APPLICATIONS

The new variety, 'Campbell Jonathan' differs from its parent and other 'Jonathan' varieties in the following characteristics:

A. The fruit of the new variety differs from previous 'Jonathan' cultivars and its parent in the boldness and coloration of the striping pattern of the fruit. 'Snyder' (U.S. Plant Pat. 2650) has a "substantially solid color"; 'Super Jon' (U.S. Plant Pat. 5,086) is "faintly striped"; 'Higgins' (U.S. Plant Pat. 6,406) has a "faint, dark red stripe"; 'Thome' (U.S. Plant Pat. 8,701) has a "dark red blush"; 'Jackson' (U.S. Plant Pat. 10,115) has "no striping"; the parent 'Robison' (U.S. Plant Pat. 2,934), has "minute faint stripes" whereas the new variety has a bold pattern of alternating dark red and lighter red stripes.

*Malus domestica*

BACKGROUND OF THE INVENTION

A new and distinct variety of Jonathan apple tree originating as a limb mutation of the *Malus domestica* variety of 'Robison', (U.S. Plant Pat. 2,934) ), hereinafter referred to as 'Campbell Jonathan'. This new sport is unique from its parent because it has a very bold pattern of alternating dark red and bright red stripes on the skin of its fruit, unlike its parent which has very faint, thin stripes.

SUMMARY OF THE INVENTION

This new and distinct variety of Jonathan apple tree was discovered at 1400 West Washington, Waverly, Mo. 64096 as a limb mutation of 'Robison', (U.S. Plant Pat. 2,934), in an orchard planted in 1986. The new variety was noticed because the fruit was boldly striped in comparison to the parent, which has little or no stripe.

Observations during the next two seasons confirmed that the fruit colored with a very bold striping pattern The mature fruit of the new variety finishes to a full red pattern of dark red and light red stripes.

In August of 1996, buds were taken from the original limb and trees for further testing were produced by cleft grafting onto existing apple trees. In August of 2006, 400 trees were produced by chip budding on 'M9 NIC 29' (an unpatented selection) rootstock in Brentwood, Calif. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained in Waverly, Mo.

FIG. 1 illustrates the fruits and foliage of the new variety at maturity.

FIG. 2 illustrates blossoms and buds of the new variety.

DETAILED BOTANICAL DESCRIPTION

A detailed description of the 'Campbell Jonathan' cultivar follows using The Royal Horticultural Society of London Colour Chart, 1986 edition, for color identification except where general color terms are sufficient.

Parentage: A limb mutation of 'Robison', (U.S. Plant Pat. 2,934). Locality of the original discovery and observations is 1400 West Washington, Waverly, Mo. 64096.

Tree:
*Age.*—10 years.
*Size.*—Large, height 4 m, width 4 m.
*Vigor.*—Vigorous, yearly growth averages 1 m.
*Density.*—medium.
*Form.*—Round, slightly weeping.
*Production.*—Very productive, averaging 800 bushels per acre.
*Growth type.*—Non-spur.
*Bearing.*—Annual.

Trunk:
*Size.*—29 cm in diameter at 90 cm above ground level.
*Surface.*—Rough.
*Bark color.*—Gray 201 B.
*Lenticels.*—Length 1 cm, width 1 cm.
*Lenticel color.*—Grayed White 156B.
*Lenticel density.*—1 to 2 per $cm^2$.

Branches:
3 *year old branch.*—10 mm in diameter, color Gray 201B, angle to 4 year old branch 30° to 45°.
2 *year old branch.*—6 mm in diameter, color Gray 201 B, angle to 3 year old branch, 30° to 50°.
1 *year old branch.*—3 mm in diameter, length 80 to 100 cm, color Grayed Orange 165D; lenticels 0.1 mm in diameter, round, color Grayed White 156D, angle to 2 year old branch, 30° to 50°.

Leaves:
*Size.*—Length 100 mm, width 60 mm.
*Texture.*—Leathery, crisp.
*Form.*—Ovate.
*Base.*—Roundly cuneate.
*Apex.*—Acute.
*Adaxial surface pubescence.*—None.
*Abaxial pubescence.*—Finely pubescent.
*Adaxial surface color.*—Yellow Green 146A.
*Abaxial surface color.*—Yellow Green 146C.
*Venation.*—pinnate, 8 to 10 veins, mainly alternate, color Yellow Green 146C.
*Margin.*—Serrate.
*Petiole length.*—45 mm.
*Petiole width.*—2 mm.
*Petiole abaxial color.*—Yellow Green 145C to Grayed Purple 185A toward base and abscission layer on larger leaves.
*Petiole groove.*—Very shallow, depth 0.01 mm.
*Stipules.*—Absent.
*Leaf glands.*—None observed.

Leaf buds:
*Length.*—1.5 mm.
*Width.*—2 mm.
*Color.*—Yellow Green 145B.
*Placement on branch.*—Applied.
*Internode distance.*—35 mm.

Spurs: Present on 2 year and older wood.
*Length.*—20 mm.
*Width.*—5 mm.
*Color.*—Grayed Orange 166A.

Flowers at popcorn stage:
*Pedicle.*—Length 3 cm, diameter 0.2 mm.
*Pedicel color.*—Green 138D
*Bud.*—Length 9 mm, width 9 mm, shape round.
*Bud color.*—Red Purple 73B to Red Purple 73C on outer surface of petals, inner surface is White 155D.

Flowers at full bloom:
*Presentation.*—Showy.
*Fragrance.*—Faint.
*Fertility.*—Fertile.
*Corolla diameter.*—3 cm.
*Numbers of flowers per cluster.*—5 to 7.

Petals:
*Arrangement.*—5 in number, length 1.5 cm to 2 cm, width 1 cm.
*Color.*—Upper surface: White 155D. lower surface: White 155D.
*Shape.*—Broad, round at tip, broadly pointed at apex, edges and tip flat, petals separate.
*Texture.*—Soft.
*Receptacle.*—Length 1 cm, width 0.5 cm, color Green 138D.
*Peduncle.*—Length 11 mm, width 1 mm, color Green 138D.
*Pedicel.*—Length 35 mm, width, 1 mm, color Green 138D.
*Sepals.*—Pointed, straight, 5 in number, length 0.5 mm, width 1 mm, color Green 138D.
*Stamens.*—20 to 23 in number, color White 155D.
*Anthers.*—Oblong in shape, size 0.01 to 0.05 mm. color Yellow 13A
*Pollen.*—Present.
*Pistil.*—Held at the same height as anthers in a majority of blossoms.
*Ovary.*—Length 0.2 mm, width 0.1 mm, color Green 138D, pubescent. Style: length 0.2 mm, width 0.01 mm, color Green 138B. Stigma: length 0.01 mm, width 0.05 mm, color Yellow 10D.

Pollination requirements: Will provide pollen for any other compatible mid-season blooming variety and requires pollen from other mid-season blooming, fertile varieties such as Gala (an unpatented selection) or Granny Smith (an unpatented selection).

Fruit:
*Maturity when described.*—Firm ripe.
*Date of picking.*—September 1$^{st}$ in Waverly, Mo. Generally harvested in one picking.
*Size.*—Axial diameter 80 mm to 90 mm, transverse diameter 90 mm to 95 mm.
*Fruit weight (firm ripe).*—220 g to 245 g.
*Form.*—Uniform, symmetrical, regular, oblate.
*Cavity.*—Acuminate, depth 15 mm, width 22 mm.
*Basin.*—Symmetrical, abrupt at base, wide, depth, 16 mm, width 30 mm.
*Calyx.*—Open, segments persistent, recurved, outer and inner surfaces pubescent.

Skin:
*Thickness.*—Thin.
*Texture.*—Very smooth, glossy with medium cuticle wax.
*Tendency to crack.*—Slight.
*Lenticels.*—Color White 155A, prominent, round, 0.5 mm in diameter, 8 to 10/$cm^{sq}$.
*Color.*—Red 53A with wide alternating stripes of Red 46A and Red 46B. Stripes average 5 mm to 10 mm in width.
*Ground color.*—Red 47A Flesh:
*Aroma.*—Sweet, aromatic.
*Color.*—Yellow White 158B.

*Texture.*—Firm, tender, fine, crisp.

*Eating quality.*—Best.

Core:

*Bundle area.*—Medium to ovate, cordate, symmetrical at base.

*Bundle.*—Inconspicuous, green, alternate above stamens.

*Carpillary area.*—Distinct, medium size.

*Calyx tube.*—Slightly urn shaped, open.

*Depth of tube to shoulder.*—20 mm.

*Styles.*—Distinct, pubescent.

*Stamens.*—One distinct whorl, small.

*Seed cells.*—Walls thin, tough, length 18 mm, width 8 mm.

*Longitudinal section.*—Broadly ovate.

Seeds:

*Number perfect.*—8 to 12.

*Number in one cell.*—2 to 4.

*Length.*—10 mm.

*Breadth.*—5 mm.

*Form.*—Obtuse, non-tufted.

*Color.*—Grayed Purple 183A.

Stem:

*Length.*—11 mm.

*Width.*—2 mm at base to 4 mm at clubbed end.

*Color.*—Yellow Green 152D.

Use: Processing, fresh market, dessert.

Shipping quality: Good, subject to stem puncture.

Keeping quality: Excellent, 90 to 120 days in common storage, 6 months in controlled atmosphere storage.

Tree winter hardiness: Average for an apple variety. Tree is hardy to −10° to −25° F.

Bud winter hardiness: −15° to −20° F., dependant on the stage of development of the bud.

Drought tolerance: Average for an apple variety. Normal requirements average ½" of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases.

I claim:

1. A new and distinct variety of apple tree, *Malus domestica*, substantially as herein shown and described.

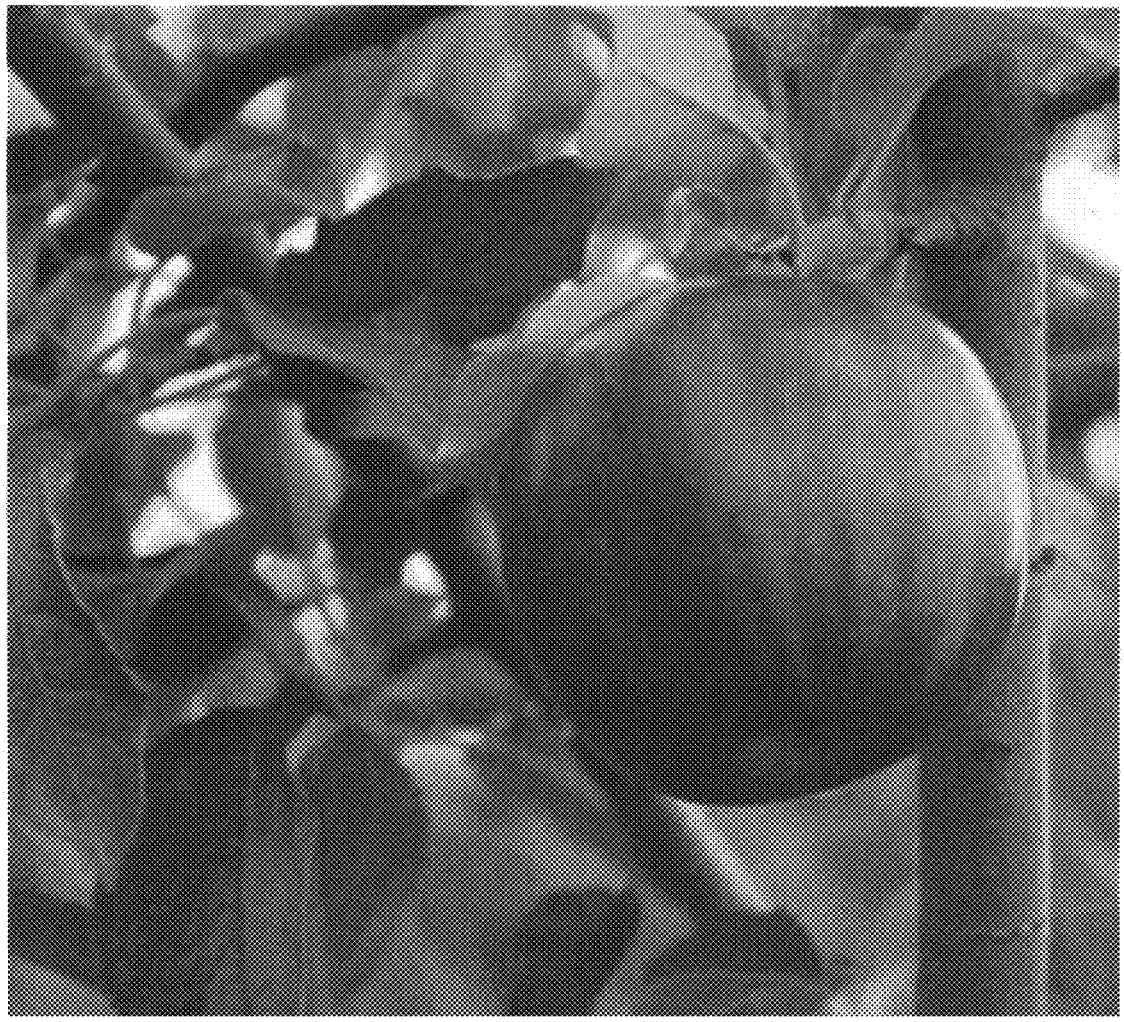

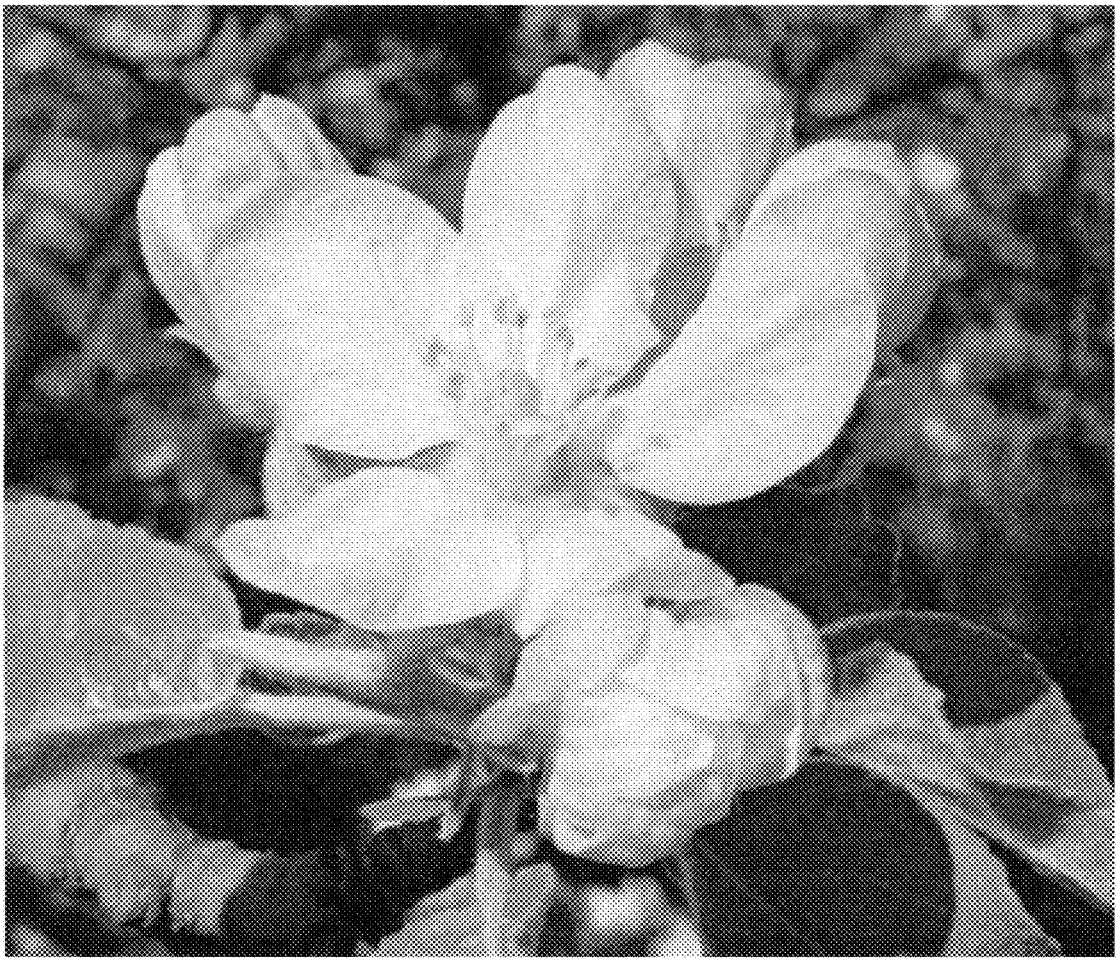

* * * * *